United States Patent
Reinhardt et al.

(10) Patent No.: US 6,254,525 B1
(45) Date of Patent: Jul. 3, 2001

(54) CARDIAC ASSIST SYSTEM AND METHOD THEREOF

(75) Inventors: Robert W. Reinhardt, Fort Salonga, NY (US); Howard R. Levin, Teaneck, NJ (US)

(73) Assignee: Cardio Technologies, Inc., Pine Brook, NJ (US)

(*) Notice: Subject to any disclaimer, the term of this patent is extended or adjusted under 35 U.S.C. 154(b) by 0 days.

(21) Appl. No.: 09/432,518

(22) Filed: Nov. 2, 1999

Related U.S. Application Data (60) Provisional application No. 60/107,015, filed on Nov. 4, 1998.

(51) Int. Cl.[7] .................................................. A61M 1/10
(52) U.S. Cl. ......................... 600/17; 623/3.27; 623/3.28; 623/3.21; 607/5; 607/3
(58) Field of Search ................ 600/16, 17; 607/2, 607/3, 4, 5; 623/3.11, 3.16, 3.21, 3.28, 3.27

(56) References Cited

U.S. PATENT DOCUMENTS

| | | | |
|---|---|---|---|
| 4,192,293 | * 3/1980 | Asrican | 600/17 |
| 4,902,272 | * 2/1990 | Milder et al. | 600/18 |
| 4,902,273 | * 2/1990 | Choy et al. | 600/18 |
| 4,925,443 | 5/1990 | Heilman et al. | 600/16 |
| 5,098,369 | 3/1992 | Heilman et al. | 600/16 |
| 5,176,619 | 1/1993 | Segalowitz | 600/18 |
| 5,800,334 | * 9/1998 | Wilk | 607/3 |

* cited by examiner

Primary Examiner—Kennedy Schaetzle
(74) Attorney, Agent, or Firm—Darby & Darby

(57) ABSTRACT

A cardiac assist system includes a sensor that is operative to sense the electrical activity of a patient's heart. The sensed electrical activity is processed to determine the onset of ventricular contraction. A compressive force from a ventricular assist device is applied to the ventricles during at least a portion of the heart's ventricular contraction. The cardiac assist system also includes an electrical stimulating system. Thus, in the event the heart begins to fibrillate, the electrical stimulating system is actuated to apply stimulating pulses to the heart.

18 Claims, 4 Drawing Sheets

CARDIAC ASSIST SYSTEM AND METHOD THEREOF

CROSS-REFERENCE TO RELATED APPLICATIONS

This application claims priority pursuant to 35 U.S.C. §119 based upon U.S. Provisional Application Ser. No. 60/107,015 filed Nov. 4, 1998, the entire disclosure of which is hereby incorporated by reference.

BACKGROUND OF THE INVENTION

1. Field of the Invention

The present invention relates to temporary therapeutic devices to work in conjunction with a diseased or failing heart to satisfy the hemodynamic needs of a patient. More particularly, the invention relates to a cardiac assist system for assisting a heart to pump blood, sensing the heart's electrical activity and, when necessary, defibrillating the heart.

2. Discussion of the Related Art

The human heart is a very complicated organ that relies on both mechanical and electrical operation to properly perform. As with any complicated mechanism, problems can and do arise, and the heart is no exception. For example, over time the electrical pathways in the heart (which sequentially cause the atria and ventricles to contract) may fail, thereby causing the heart to lose its rhythm, which is known as arrhythmia. In that event, the ventricles will contract at improper times, and as a result the output of blood decreases.

Diseased hearts may also fibrillate, which results in rapid and irregular contractions of the muscle fibers of the heart. Furthermore, in some failing hearts the heart muscle is no longer able to contract the ventricles to a sufficient extent, also resulting in a dangerous reduction in the amount of blood flow. Thus, the problem in a diseased heart may be mechanical, electrical, or a combination of both.

Numerous attempts have been made to assist these diseased or failing hearts by applying external pressure directly to the heart. One such example is direct manual compression of the heart by a person's hand during open chest cardiopulmonary resuscitation. Often, however, the patient requires cardiac or circulatory support for extended periods of time, such as hours, days, or even weeks, and it is quite difficult for medical personnel to apply a rhythmic pulsating pressure for such an extended period of time. Further, it is difficult if not impossible to apply by hand a uniform compressing force to a significant portion of the exterior ventricle surface of the chamber of the heart. Moreover, the chest should not be opened for extended periods of time because of the increased risk of infection. As such, manual manipulation of the heart is not a solution to the problem in most cases.

To overcome this problem, mechanical devices have been developed to apply external pressure directly to the heart. Some of these devices utilize an inflatable liner that surrounds the heart. For example, U.S. Pat. No. 5,119,804 to Anstadt discloses a cup that is provided with an elastomeric liner. The heart is held in place within the liner, which is cyclically inflated and deflated to apply external pressure to the heart. While this device provides an improvement in hemodynamics for a diseased or failing heart, the device nevertheless suffers from shortcomings, one being the fact that only a fraction of the external fluid pressure that is applied in the cup inlet to displace the liner, which in turn displaces the heart wall, is transmitted to the heart itself to assist the heart to pump blood. As the liner is inflated, because of its axial length limitation, it stretches and bulges radially inwardly. Thus, the transmural pressure of the liner is directed in the radially outward direction (i.e., away from the heart), such that the pressure applied to the heart is less than the pressure applied to the liner. In addition, due to the bulging of the liner, the heart is deformed into a generally hour-glass shape. Thus, there is not a uniform application of pressure to the outer walls of the ventricles. Therefore, a relatively high pressure must be applied within the liner (e.g., 150–200 mm Hg) to support circulation.

Another shortcoming inherent in the prior art devices results from the fact that relatively high pressures are applied almost exclusively to the central portion of the ventricles' outer surfaces. This causes the heart to deform into an unnatural shape and may even eventually cause trauma (e.g., bruises) to the heart, especially if one of those devices is operated for an extended period of time.

In addition, it has been found that these inflatable devices can act as electrical insulators to insulate the heart from externally applied energy, such as the energy from defibrillation paddles. Therefore, when such a device is in place over the heart (which can be on the order of days or even weeks), the heart in many instances cannot be defibrillated. It is believed that the polymer material of the liner device and the air in the liner when it is inflated act as insulators around the heart, preventing the defibrillation current from reaching the heart. Thus, while such devices provide a benefit in the form of mechanically assisting the heart to pump blood, those devices can impede electrical aid from reaching the heart.

Accordingly, it will be apparent that there continues to be a need for a cardiac assist system that automatically applies a compressive force to the ventricles during ventricular contraction to assist the ventricles to pump blood, and that also is operable to electrically stimulate the heart during fibrillation and the like. The present invention addresses these needs.

SUMMARY OF THE INVENTION

Briefly, and in general terms, the present invention is directed to a system and method for providing mechanical and/or electrical stimulation to the heart when necessary. The system comprises a ventricular assist device which is designed for extension over at least a portion of the heart, and operative to intermittently apply a compressive force to the heart to assist the heart in pumping blood. The system also includes an electrical stimulating subsystem including one or more stimulating electrodes placed at selected locations to come into close proximity to, or engagement with, the heart. The stimulating electrodes are responsive to receipt of electrical stimulating energy to apply the energy to the heart. The system still further includes a heart sensor which senses the electrical activity of the heart and generates corresponding electrical signals. A controller is electrically connected to the sensor and to a source of pressurized air, and is responsive to receipt of the electrical signals from the sensor to determine the onset of ventricular contraction and to control the source of pressurized air to inflate the ventricular assist device synchronous with the ventricular contraction of the heart.

Thus, in one illustrative embodiment the cardiac assist system of the present invention comprises: a ventricular assist device including a suction membrane configured to engage the heart and an inflatable bladder that is operative to apply pressure to at least a portion of the heart; a source of pressurized air is connected to the inflatable bladder and is operative to inflate the bladders; at least one electrical sensor is in contact with the suction membrane and is configured to be positioned in contact with the heart when the ventricular assist device is engaged to the heart, the electrical sensor being operative to sense electrical activity of the heart and to generate corresponding electrical signals; and a controller is electrically connected to the sensor and to the source of pressurized air, the controller being programmed to receive the electrical signals from the sensor, to determine from the electrical signals when the heart is in ventricular contraction, and to control the source of pressurized air to supply pressurized air to the bladder to inflate the bladder during at least a portion of the ventricular contraction of the heart.

In another illustrative embodiment, the present invention is directed to a method of assisting a heart to pump blood, comprising: engaging a ventricular assist device to at least a portion of the heart; sensing the electrical activity of the heart; determining when the heart engages in ventricular contraction; and applying pressure to at least a portion of the ventricles of the heart coinciding with the ventricular contraction of the heart.

BRIEF DESCRIPTION OF THE DRAWINGS

The above and still further objects, features and advantages of the present invention will become apparent upon consideration of the following detailed description of specific embodiments thereof, especially when taken in conjunction with the accompanying drawings wherein.

DETAILED DESCRIPTION OF THE PREFERRED EMBODIMENTS

Figure 1:
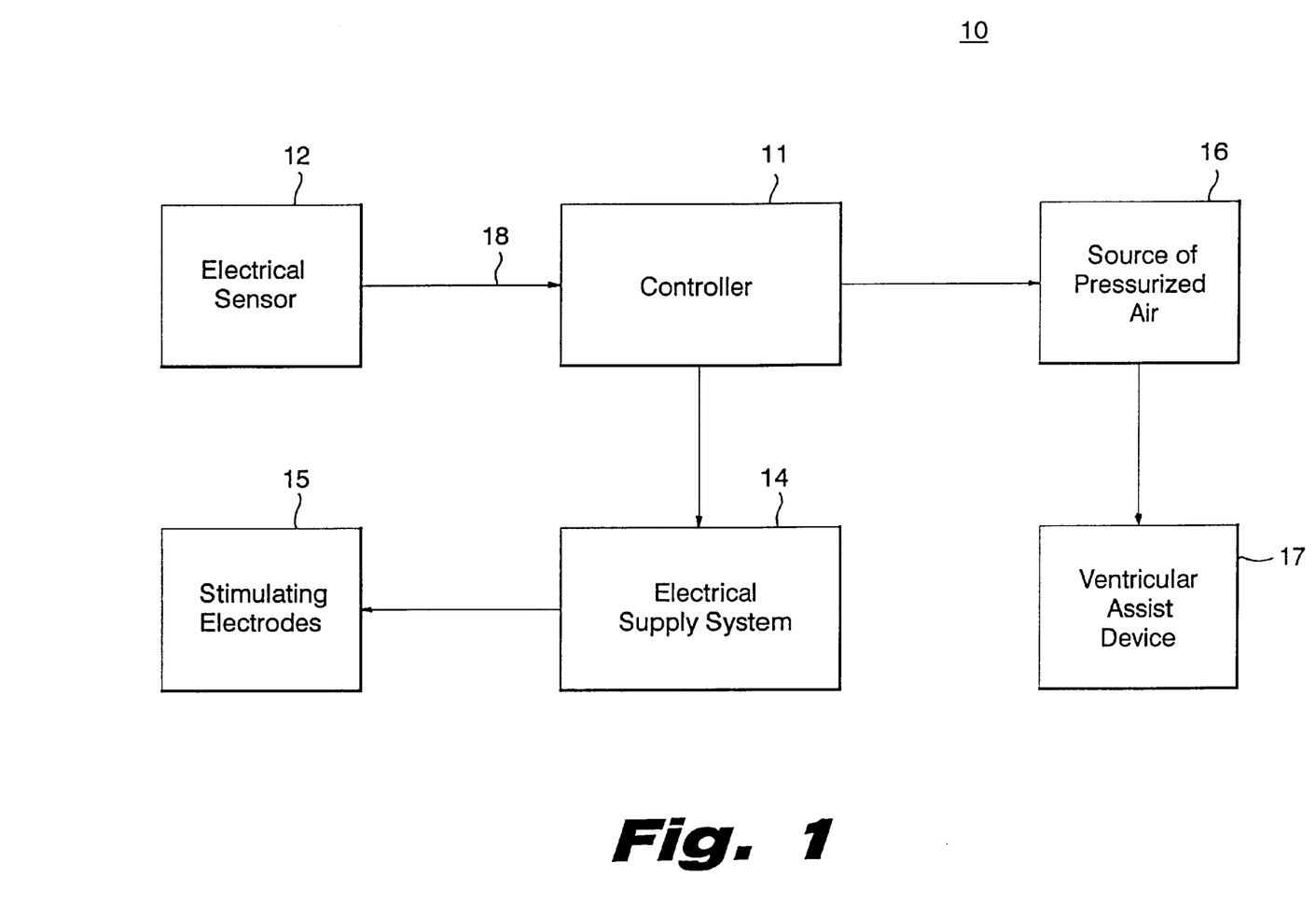
FIG. 1 is a block diagram of one illustrative embodiment of a cardiac assist system according to the present invention.

Referring now to FIG. 1, one illustrative embodiment of a cardiac assist system 10 is shown. The cardiac assist system comprises a controller 11, an electrical sensor 12, an electrical supply system 14, one or more stimulating electrodes 15, a source of pressurized air 16, and a ventricular assist device (or cuff) 17. The system is operative to sense the heart's electrical activity for the purpose of determining the onset of ventricular contraction, and is further operative to assist the heart in contracting during ventricular contraction to increase the amount of blood output by the heart.

In addition, when the heart begins to fibrillate or otherwise requires the application of one or more stimulating pulses, the system 10 may be signaled, for example, by a clinician, and responds with an electrical stimulation pulse applied to the heart to regain normal sinus rhythm of the heart.

Figure 3:
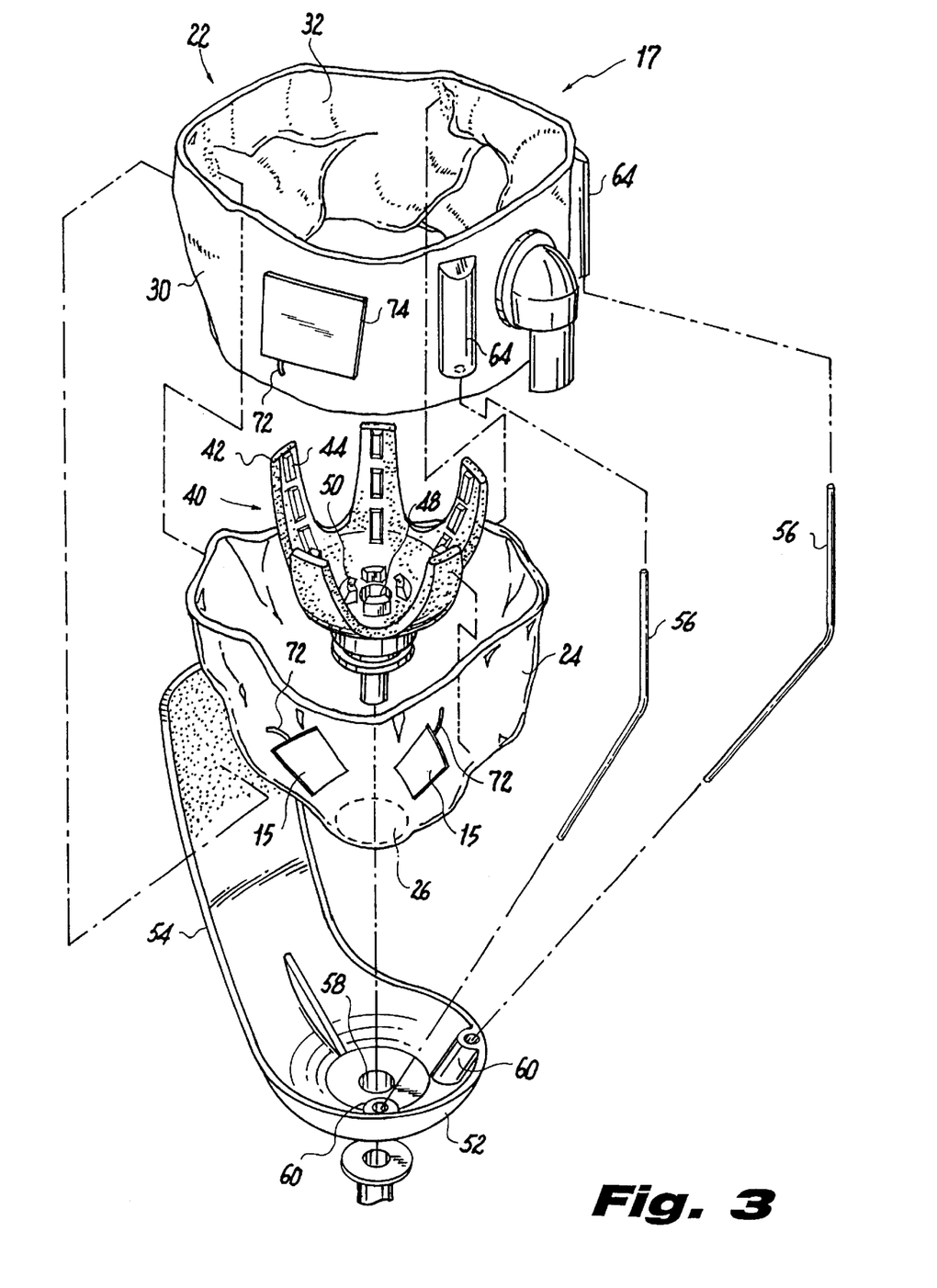
FIG. 3 is a perspective view showing one illustrative embodiment of a ventricular assist device and electrical system included in the cardiac assist system of the present invention.

Referring to FIGS. 1 and 3, the system 10 includes one or more electrical sensors 12, which may take many different forms. In one illustrative embodiment, the electrical sensor comprises a conventional electrode configured for placement against or in close proximity to the patient's heart. As described in greater detail below, the electrode may be mounted on or placed against an inside surface of the ventricular assist device 17 for reliable placement against the patient's heart. The electrode is connected to a lead wire 18 which conducts the electrical signals corresponding to the heart's electrical activity from the sensor to the controller 11 for processing, as described in greater detail below.

The system 10 further includes the electrical supply system 14 which is electrically connected to the stimulating electrodes 15, and which preferably comprises a pulse generator or the like that is operative to generate electrical stimulating pulses. As is shown in FIG. 1, in one illustrative embodiment the electrical supply system is electrically connected to, and controlled by, the controller 11. For example, when a clinician desires to apply a stimulating pulse to the heart, such as when the heart is fibrillating, the clinician may simply press a button (not shown) on the controller to signal the controller, which in turn transmits a corresponding control signal to the electrical supply system to cause the electrical supply system to generate a stimulating pulse.

While the electrical supply system 14 is shown and described being electrically connected to the controller 11, it will be apparent to those skilled in the art that it is not necessarily connected to the controller. The electrical supply system can alternatively be in the form of a stand-alone device which is not in communication with the controller 11, and which is controlled by the clinician when the patient's heart fibrillates by simply pressing a button or the like associated with the electrical supply system.

Referring to FIG. 1, the system further includes one or more stimulating electrodes 15 electrically connected to the electrical supply system 14. The stimulating electrodes are configured for placement in close proximity to, or in contact with, the heart, and are operative to receive the stimulating pulses from the electrical supply system and to apply the stimulating pulses to the heart tissue. The stimulating electrodes may be mounted to an inside surface of the ventricular assist device 17, or may simply be placed against the heart tissue, with the ventricular assist device then extended over the heart and stimulating electrodes to sandwich the stimulating electrodes between the ventricular assist device and the heart.

Preferably, the system 10 comprises two or more stimulating electrodes 15 (FIG. 3), with one (or more) of the stimulating electrodes defining a high-potential electrode, and the other defining a ground (or low-potential) electrode. Thus, the electrical stimulating pulses from the electrical supply system 14 are conducted to the high-potential electrode, are applied through the heart to the low-potential electrode, and are conducted back to the electrical supply system.

Several forms of the electrical supply system 14 and stimulating electrode configuration are shown in co-pending U.S. Provisional Patent Application Ser. No. 60/104,429, filed on Oct. 15, 1998, and assigned to the assignee of the present invention, the disclosure of which is incorporated herein by reference in its entirety.

Figure 2:
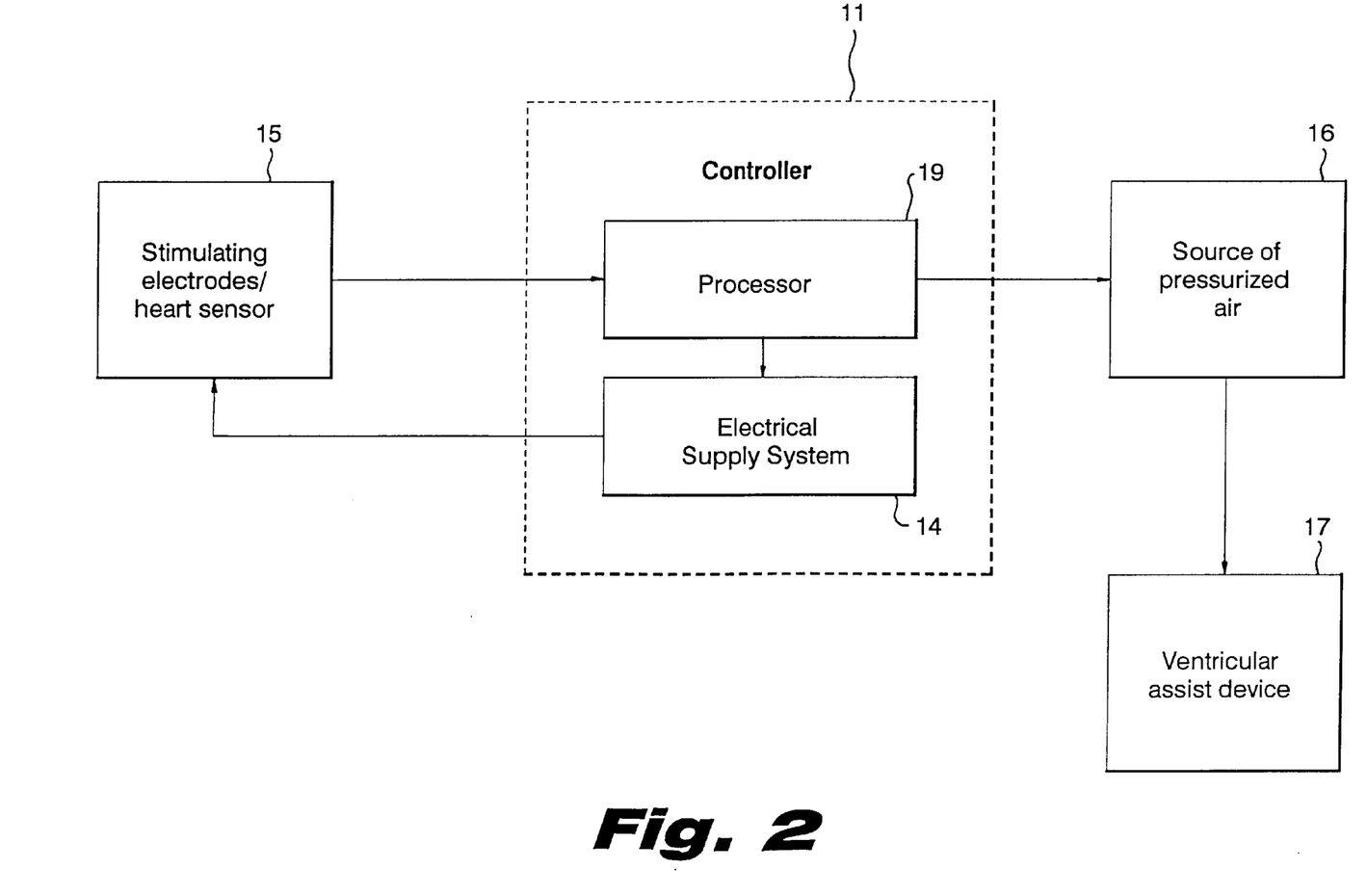
FIG. 2 is a block diagram of another illustrative embodiment of the cardiac assist system of the present invention.

In a preferred embodiment, one or more of the stimulating electrodes 15 also serve as the electrical sensor 12 (FIG. 2). Thus, the one or more stimulating electrodes are electrically connected to both the electrical supply system 14 and to a processor 19 of the controller 11 (FIG. 2), for selectively sensing the heart's electrical activity and applying stimulating pulses to the heart tissue. During periods of non-fibrillation (i.e., when the heart does not require stimulating pulses), the stimulating electrode functions as a heart sensor, monitoring the heart's electrical activity and transmitting corresponding electrical signals to the processor 19. As described in greater detail below in connection with FIG. 4, the electrical signals are processed to determine when the heart generates an R-wave, corresponding to the onset of ventricular contraction.

Conversely, in instances where the heart is fibrillating, the processor 19 may be signaled by the clinician to control the electrical supply system 14 to generate one or more stimulating pulses, which are conducted to one or more of the stimulating electrodes 15 for application to the heart in order to stimulate the heart.

Referring to FIG. 3, there is shown one illustrative embodiment of the ventricular assist device 17 and stimulating electrodes 15 included in the cardiac assist system 10 of the present invention. The illustrative embodiment of the ventricular assist device 17 shown in FIG. 3 is described in greater detail in co-pending U.S. Provisional Patent Application Ser. No. 60/098,130, entitled "METHOD AND APPARATUS FOR ASSISTING A HEART TO PUMP BLOOD", and filed on Aug. 27, 1998, (D&D Docket Number 1099/0D812), assigned to the assignee of the rights in the present invention, the disclosure of which is hereby expressly incorporated by reference. It will be apparent that the cardiac assist system 10 of the present invention can incorporate any suitable ventricular assist device, for example, the other types of ventricular assist devices shown in the above-mentioned and expressly incorporated patent applications, and that the ventricular assist device 17 shown in the figures is exemplary of one such device. In general, the ventricular assist device (or cuff) comprises an upwardly opening receptacle defining an interior chamber 20 sized for making a relatively close fit about at least a portion of a patient's heart. The chamber is defined by an annular inflatable bladder 22 and an upwardly opening suction membrane 24 disposed inwardly of the bladder. The suction membrane includes a central opening 26 (FIG. 3) formed in the lower end thereof that is engaged to one end of a vacuum tube (not shown) for fluid communication therebetween. The other end of the vacuum tube is connected to a vacuum source (not shown) that is operative to draw air through the vacuum tube. The suction membrane is preferably connected at its upper end to the upper end of the bladder by means of UV adhesive, cyanoacrylate, heat sealing, or other suitable means. Thus, the cuff may be extended over the ventricles of the heart, the vacuum tube connected to the vacuum source, and the vacuum source actuated to withdraw air from the chamber 20 to create a partial vacuum within the chamber, which causes the suction membrane to be drawn radially inwardly and into secure engagement with the heart to engage the ventricular assist device to the heart.

The bladder 22 is preferably made from a combination of biocompatible, reinforced and non-reinforced polyurethane, or other elastic polymers. In one embodiment the polyurethane defines a fluid impermeable layer that is reinforced with a non-stretchable reinforcing layer, for example, a polyester weave. The outer wall 30 of the bladder is preferably thicker, stiffer, or of a higher durometer than the bladder's inner wall 32 to resist radial outward expansion of the bladder. The outer wall is further formed with one or more openings 33 (FIG. 3) that are in fluid communication with first ends of respective flexible fluid lines 34. The respective second ends of the fluid lines are connected to one or more sources of pressurized fluid (not shown) to selectively inflate the bladder. In the illustrative embodiment shown, when the bladder is deflated the inner wall of the bladder folds in upon itself while remaining in relatively close proximity to the heart. Then, as the bladder is inflated, the inner wall at least partially unfolds as it is driven radially inwardly to uniformly engage the portion of the heart that is contained within the cuff 17. In this manner, the bladder need not stretch to engage the heart, resulting in a substantially uniform application of force to the ventricle outer walls, without any significant loss due to transmural pressure in the inner wall of the bladder, because the bladder is not stretched as it is inflated. In addition, because the bladder does not stretch, the heart is not contorted into a generally hourglass shape when the bladder is inflated and comes into contact with the heart.

The ventricular cuff 17 further includes a flexible cleated finger assembly 40 for releasably engaging the outer surface of the heart (FIG. 3). The flexible cleated finger assembly is disposed inwardly of the suction membrane 24, such that when the suction membrane is drawn inwardly against the heart, the fingers are driven into contact with the patient's heart. The finger assembly is preferably molded of a very flexible polymer, such as polyurethane, silicone, TPE, etc., and is connected to the inner surface of the suction membrane 24 by means of a UV adhesive, cyanoacrylate, adhesive, heat sealing, or other suitable means. The finger assembly includes plural fingers 42, for example five, each of which includes plural projecting cleats 44 to engage the outer surface of the heart. The finger assembly further includes a base 46 engaged to the suction membrane 24 and formed with a central opening 48 aligned with the opening in the suction membrane for fluid communication therethrough. The base also includes plural raised cleats 50 which surround the opening 48 to prevent the heart tissue from plugging the opening when the vacuum source is actuated. The cleats and fingers cooperate to define plural fluid flow paths to allow fluid to be drawn from substantially the entire chamber through the vacuum line 28. In this manner, the holding force is distributed over a large portion of the surface of the heart rather than being concentrated at the apex of the heart, resulting in a more secure engagement of the cuff to the patient's heart without a large force being applied to a small area of the heart.

The ventricular cuff 17 further includes an apical reinforcing support assembly including a spatula 52, a backplate reinforcement 54, and a pair of supporting rods 56. The spatula is preferably formed of semi-rigid polymer such as in polyurethane, silicone, TPE, etc. that is securely engaged to the bottom ends of both the finger assembly 40 and the suction membrane 24. The spatula thus serves to hold the finger assembly and suction membrane in place relative to the bladder 22. The spatula is formed with a central opening 58 for extension therethrough of the vacuum line.

The backplate reinforcement 54 is preferably formed integral with the spatula 52 and is also preferably formed of semi-rigid polyurethane, silicone, TPE, etc. The backplate reinforcement is connected to the outer wall of the bladder 22 by means of a layer of adhesive, by heat sealing, or the like. The backplate is designed for alignment with the inferior portion of the heart, and thus the portion of the bladder aligned with the backplate is preferably not inflatable.

The supporting rods or stylettes 56 are in the form of curved segments of a non-flexible material such as titanium, stainless steel, polycarbonate, or the like. The respective bottom ends of the rods are received in respective upwardly opening receptacles 60 formed in the spatula 52. The rods angle upwardly and outwardly from the spatula, and then turn to extend upwardly and terminate in respective upper ends that are received in respective stylette caps 64 that are bonded to the outer wall of the bladder 22 by means of adhesive or the like. The receptacles are preferably formed of a flexible polymer, such as polyurethane, silicone, TPE, etc. or the like. The rods are preferably spaced approximately 90°–120° apart. The rods provide support for the bladder as the bladder and suction membrane 24 are extended over the heart, and cooperate with the backplate reinforcement to facilitate extension of the bladder and suction membrane over the heart.

Still referring to FIG. 3, the stimulating electrodes 15 are shown in place against an inside surface of the suction membrane 24. In this manner, when the suction membrane attaches to the heart, the stimulating electrodes are sandwiched between the suction membrane and heart tissue, and cannot move relative to the heart. Therefore, the stimulating electrodes serve as reliable sensors of the heart's electrical activity, in addition to being operable to apply stimulating pulses to the heart. The stimulating electrodes are connected to respective wires 72, which preferably comprise multi-lead wires for connection to both the controller 11 and to the electrical supply system 14, for, respectively, transmitting electrical activity signals from the electrodes and transmitting stimulating pulses to the electrodes.

In one illustrative embodiment, the cardiac assist system 10 further includes one or more pick-up electrodes 74 which define components of the electrical supply system 14 and are connected to the respective stimulating electrodes 15 via the wires 72 (FIG. 3). In one illustrative embodiment, the pick-up electrodes are mounted on the outside surface of the ventricular assist device 17 and serve to collect externally applied electrical energy and to conduct the collected energy to the stimulating electrodes for application to the patient's heart. The pick-up electrodes are described in greater detail in co-pending U.S. Provisional Patent Application Ser. No. 60/104,429, filed Oct. 15, 1998, entitled "PASSIVE DEFIBRILLATION ELECTRODES FOR USE WITH CARDIAC ASSIST DEVICE", the disclosure of which is hereby incorporated by reference.

Figure 4:
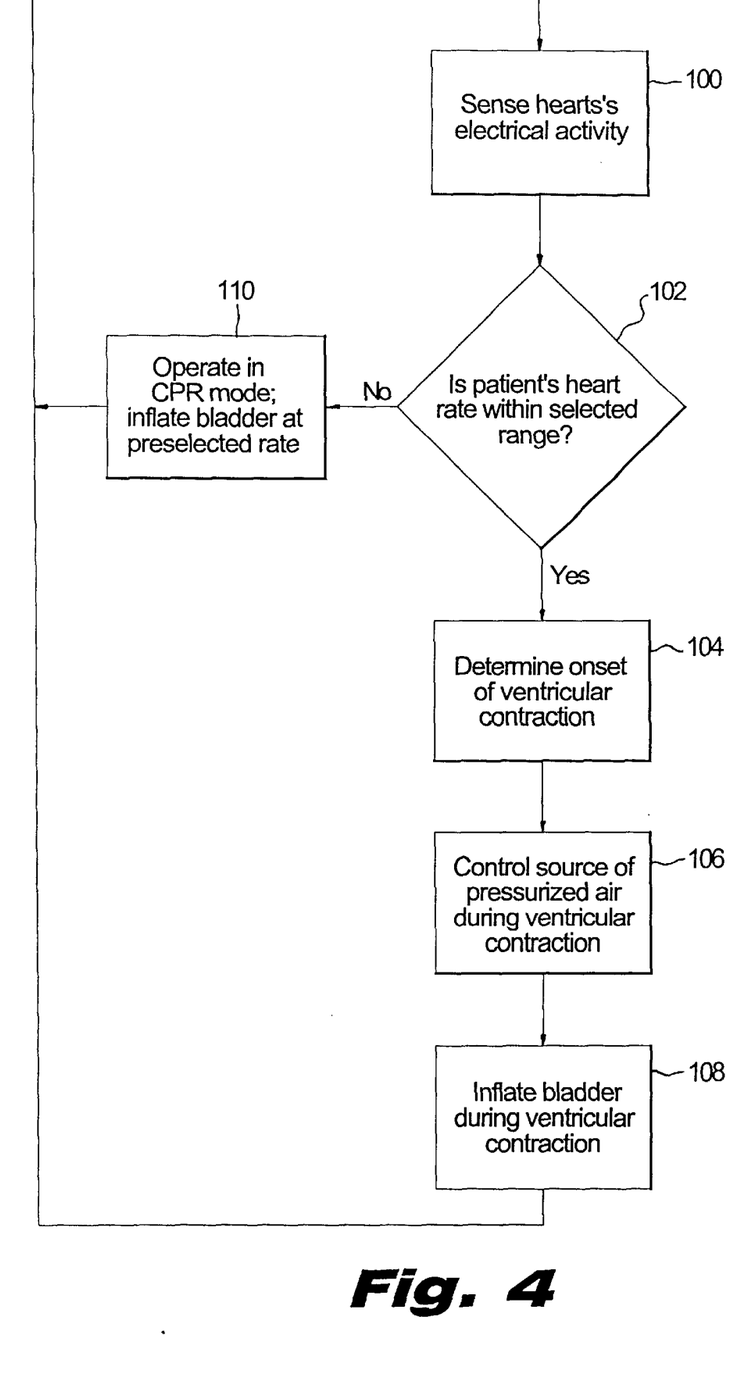
FIG. 4 is a flowchart depicting the operational flow of a controller included in the cardiac assist system of the present invention.

Referring now to FIG. 4, the operation of the controller 11 is described in detail. Initially, the electrical sensor 12 senses the heart's electrical activity and transmits corresponding electrical signals to the controller 11, at step 100. As described above, the electrical sensor is preferably an electrode (e.g., one of the stimulating electrodes 15). Thus, the sensor senses the electrical activity of the heart and generates corresponding electrical signals with intensities corresponding to the intensity of the sensed electrical activity. At step 102, the controller 11 determines whether the patient's heart rate is within some preselected range. This is done by determining the interval between successive R-waves, T-waves, or other suitable occurrence in the electrocardiogram. As described above, the controller is preferably programmed to detect R-waves by comparing the sensed signals with a preselected constant or dynamic threshold value.

If the patient's heart rate is within the preselected range, then operation proceeds to step 104, and the controller processes the subsequent electrical signals from the sensor to determine the onset of ventricular contraction. In one illustrative embodiment, this is achieved by determining whether the value of the sensed signal exceeds a preselected, constant threshold value. As is well known to those skilled in the art, the magnitude of an R-wave in an electrocardiogram is much larger than the other waves, for example, the P-, Q-, S- and T-waves. Thus, the controller 11 can be programmed with a threshold value which is only exceeded during the rising R-wave, which also corresponds to ventricular contraction. Alternatively, the controller may be programmed with a dynamic threshold so that the controller does not false trigger due to pacing spikes and other far-field effects. Such a system is disclosed in co-pending U.S. Provisional Patent Application Ser. No. 60/093,918, entitled "DIGITAL ECG DETECTION SYSTEM", filed Jul. 23, 1998, assigned to the assignees of the present invention, the disclosure of which is hereby incorporated by reference.

In any event, once the controller 11 determines that the magnitude of the sensed signal exceeds the preselected threshold, operation proceeds to step 106, and the controller transmits a control signal to the source of pressurized air 16 to activate it. Activation of the source of pressurized air results in a quantity of pressurized air being conducted to the bladder 22, thereby inflating it and causing the bladder to expand radially inwardly to apply a compressive force to the ventricles during at least a portion of the ventricular contraction of the heart, at step 108. Therefore, the cardiac assist system 10 monitors the heart's electrical activity and mechanically assists the heart to pump a greater quantity of blood during each heart beat. Operation then flows back to step 100 to sense the next R-wave.

The above description is of the cardiac assist system 10 operating in an "assist mode", where inflation occurs synchronous with the native heart's ventricular contraction. In some instances, the system 10 must be operated in a "CPR mode", where inflation occurs at a fixed rate, and is not necessarily synchronous with the heart's contractions. In the CPR mode, the controller is programmed to transmit control signals to the source of pressurized air 16 at predetermined intervals, regardless of when the heart's ventricles are actually contracting. Thus, if at step 102, the patient's heart rate is determined to not be within the preselected range (e.g., if the patient's heart rate is too high (tachycardia) or non-existent), operation instead proceeds to step 110, and the system 10 is switched to the CPR mode. In the CPR mode, the controller 11 controls the source of pressurized air 16 at preselected intervals, regardless of the patient's heart rate. For example, during tachycardia, the patient's heart beats at a rapid, irregular rate. The system is operative to contract the ventricles at the preselected rate, in an effort to return the heart to normal sinus rhythm.

It will be apparent that the control signals from the controller 11 may be in the form of pulses having predetermined durations coinciding with the time duration for inflating the bladder 22. Alternatively, the source of pressurized air may be programmed to be responsive to a control pulse to deliver pressurized air to the bladder for a predetermined amount of time and then to evacuate the pressurized air from the bladder.

In use, the ventricular assist device 17 is connected to the source of pressurized air 16, and the sensor 12 is electrically connected to the controller 11. The sensor may be mounted on the inside surface of the suction membrane 24 or at some other suitable location on the inside surface of the ventricular assist device. Alternatively, the sensor may be separated from the ventricular assist device and placed against the heart tissue, with the ventricular assist device then extended over the heart to sandwich the sensor between the heart and the suction membrane. In any event, with the ventricular assist device extended over the patient's heart, a negative pressure is applied to the inside of the ventricular assist device to secure the suction membrane 24 and thus the ventricular assist device to the heart. The system 10 is then in an "attach" mode, and is ready to assist the heart.

With the sensor 12 in place against the heart tissue, the heart's electrical activity is sensed, and transmitted as a continuous analog electrical signal to the controller 11 via wire 18. The controller processes the electrical signal to determine when the heart's ventricles are contracting. When the heart's ventricles begin to contract, the controller transmits a control signal to the source of pressurized air, which delivers pressurized air for a predetermined amount of time to the bladder 22, and then evacuates the pressurized air from the bladder. In one embodiment, the controller supplies electrical power to the source of pressurized air for the predetermined amount of time to activate it, and then cuts off the supply of electrical power to the source of pressurized air to deactivate it and thereby deflate the bladder.

If the heart begins to fibrillate, the clinician presses a button or otherwise signals the controller, which transmits a corresponding control signal to the electrical supply system 14. Alternatively, in the case of a discrete electrical supply system, the clinician may press a button connected to the electrical supply system. In either case, the electrical supply system generates a stimulating pulse and conducts the pulse to the stimulating electrodes 15 to stimulate the heart.

In the case of tachycardia or no detectable heart beat, the controller is programmed to automatically determine these conditions and to enter the CPR mode to contract the ventricles at a preselected rate.

The controller 11 may also be programmed to, after a predetermined duration of operation in the "assist" mode, begin to wean the patient off of the system 10. In this mode, instead of assisting the heart during every beat, the controller actuates the source of pressurized air 16 every other beat, every fourth beat, or the like. In addition, the controller 11 may be programmed to transmit a different control signal to the source of pressurized air to reduce the quantity of pressurized air delivered to the bladder 22 and thus the augmentation pressure.

From the foregoing, it will be apparent that the cardiac assist system 10 of the present invention monitors the heart's electrical activity, determines the onset of ventricular contraction, and supplies mechanical assistance to assist the heart to assist the heart in pumping blood. In addition, should the patient's heart begin to fibrillate or otherwise require electrical stimulation, the cardiac assist system is operative to apply one or more stimulating pulses to the heart to stimulate it.

While the invention has been particularly shown and described with reference to illustrative embodiments thereof, it will be understood by those skilled in the art that various changes in form and details may be made therein without departing from the spirit and scope of the invention. Accordingly, it is not intended that the invention be limited, except as by the appended claims.

What is claimed is:

1. A system for assisting a heart to pump blood, the system comprising:
   a ventricular assist device having an interior surface and including an inflatable bladder that is operative to apply pressure to at least a portion of the heart;
   a source of pressurized fluid connected to the inflatable bladder and operative to inflate the bladder;
   at least one electrical sensor configured to be positioned in contact with the heart when the ventricular assist device is engaged to the heart, the electrical sensor being operative to sense electrical activity of the heart and to generate corresponding electrical signals; and
   a controller electrically connected to the sensor and to the source of pressurized fluid, the controller being programmed to receive the electrical signals from the sensor, process the electrical signals to determine the onset of ventricular contraction in the heart, and control the source of pressurized fluid to supply pressurized fluid to the bladder to inflate the bladder at a time synchronous with the ventricular contraction of the heart;
   wherein the sensor comprises an electrode operative to sense electrical activity of the heart and to generate a corresponding electrical signal:
   the sensor defines a stimulating electrode connected to the interior surface of the ventricular assist device to contact the heart when the ventricular assist device is placed over the heart, the stimulating electrode being responsive to receipt of electrical stimulating energy to apply the energy to the heart, the stimulating electrode further being operative to sense electrical activity of the heart; and
   further including at least one pick-up electrode external of the ventricular assist device and electrically connected to the stimulating electrode, the pick-up electrode being operative to collect electrical energy and to conduct the electrical energy to the stimulating electrode.

2. The system of claim 1, wherein the pick-up electrode is mounted on an exterior surface of the ventricular assist device.

3. The system of claim 1, further including plural pick-up electrodes and plural stimulating electrodes, the pick-up electrodes being electrically connected to the respective stimulating electrodes.

4. The system of claim 1, wherein the pick-up electrode is spaced from the ventricular assist device.

5. The system of claim 1, wherein the ventricular assist device further comprises a suction membrane configured to engage the heart, and the stimulating electrode is mounted on the suction membrane.

6. The system of claim 1, wherein the stimulating electrode is connected to a source of stimulating energy via an electrical lead.

7. A method of assisting a heart to pump blood, comprising:
   engaging a ventricular assist device to at least a portion of the heart;
   sensing the electrical activity of the heart;
   determining when the ventricles of the heart are contracting;
   applying pressure to at least a portion of the ventricles of the heart at a time synchronous with the heart's natural contraction of the ventricles; and
   applying defibrillation energy to a patient from a location external to the patient, when the patient's heart is fibrillating;
   receiving the externally applied energy at one or more electrodes inside the patient's body; and
   conducting the received energy to one or more electrodes in contact with the patient's heart to apply the energy to the heart.

8. The method of claim 7, wherein the step of applying defibrillation energy includes using defibrillation paddles.

9. The method of claim 7, wherein the step of receiving the externally applied energy includes using a pair of pick-up electrodes.

10. The method of claim 7, wherein the step of conducting the received energy includes using a pair of stimulation electrodes in contact with the heart.

11. The method of claim 7, wherein the step of determining when the ventricles are contracting comprises detecting a magnitude of electrical activity of the heart, comparing the magnitude of the detected electrical activity with a preselected threshold value, and determining whether the magnitude of the detected electrical activity exceeds the preselected threshold value.

12. A system for assisting a heart to pump blood and for applying stimulating pulses to the heart, the system comprising:

a ventricular assist device including an inflatable bladder that is operative to apply pressure to at least a portion of the heart;

a source of pressurized fluid connected to the inflatable bladder and operative to inflate the bladder;

at least one electrical sensor in contact with the ventricular assist device and configured to be positioned in contact with the heart when the ventricular assist device is engaged to the heart, the electrical sensor being operative to sense electrical activity of the heart and to generate corresponding electrical signals;

a controller electrically connected to the sensor and to the source of pressurized fluid, the controller being programmed to receive the electrical signals from the sensor, determine from the electrical signals when the heart enters into a ventricular contraction stage, and control the source of pressurized fluid to supply pressurized fluid to the bladder to inflate the bladder during at least a portion of the ventricular contraction of the heart;

a stimulating electrode in contact with the ventricular assist device and configured to be positioned in contact with the heart when the ventricular assist device is engaged to the heart; and a source of stimulating pulses in communication with the stimulating electrode and operative to generate electrical stimulating pulses and transmit the stimulating pulses to the stimulating electrode for application to the heart;

wherein the source of stimulating pulses comprises at least one pick-up electrode external of the ventricular assist device and electrically connected to the stimulating electrode, the pick-up electrode being operative to collect externally applied electrical energy and conduct the electrical energy to the stimulating electrode.

13. The system of claim 12, wherein the sensor comprises an electrode operative to sense electrical activity of the heart and to generate a corresponding electrical signal.

14. The system of claim 12, wherein the sensor defines the stimulating electrode.

15. The system of claim 12, wherein the pick-up electrode is mounted on an exterior surface of the ventricular assist device.

16. The system of claim 12, further including plural pick-up electrodes and plural stimulating electrodes, the pick-up electrodes being electrically connected to the respective stimulating electrodes.

17. The system of claim 12, wherein the pick-up electrode is spaced from the ventricular assist device.

18. The system of claim 12, wherein the ventricular assist device further comprises a suction membrane configured to engage the heart, and the stimulating electrode is mounted on the suction membrane.

* * * * *